(12) United States Patent
Wu et al.

(10) Patent No.: US 11,348,369 B2
(45) Date of Patent: May 31, 2022

(54) SERVICE CONTROL AND USER IDENTITY AUTHENTICATION BASED ON VIRTUAL REALITY

(71) Applicant: Advanced New Technologies Co., Ltd., George Town (KY)

(72) Inventors: Jun Wu, Hangzhou (CN); Huanmi Yin, Hangzhou (CN); Feng Lin, Hangzhou (CN)

(73) Assignee: Advanced New Technologies Co., Ltd., Grand Cayman (KY)

( * ) Notice: Subject to any disclaimer, the term of this patent is extended or adjusted under 35 U.S.C. 154(b) by 320 days.

(21) Appl. No.: 15/819,041

(22) Filed: Nov. 21, 2017

(65) Prior Publication Data

US 2018/0150691 A1 May 31, 2018

(30) Foreign Application Priority Data

Nov. 29, 2016 (CN) .......................... 201611079020.8

(51) Int. Cl.
*G06K 9/00* (2022.01)
*G06V 40/18* (2022.01)
(Continued)

(52) U.S. Cl.
CPC .......... *G06V 40/197* (2022.01); *A61B 3/0008* (2013.01); *A61B 3/0025* (2013.01);
(Continued)

(58) Field of Classification Search
CPC . H04W 48/14; H04N 21/254; H04N 21/2541; H04N 21/25816;
(Continued)

(56) References Cited

U.S. PATENT DOCUMENTS 2,528,010 A 10/1950 Lothman
6,526,160 B1 * 2/2003 Ito ...................... G06K 9/00597
382/117

(Continued)

FOREIGN PATENT DOCUMENTS

CN 101904106 12/2010
CN 103455746 12/2013
(Continued)

OTHER PUBLICATIONS

Crosby et al., "BlockChain Technology: Beyond Bitcoin," Sutardja Center for Entrepreneurship & Technology Technical Report, Oct. 16, 2015, 35 pages.

(Continued)

*Primary Examiner* — Jefferey F Harold
*Assistant Examiner* — Timothy R Newlin
(74) *Attorney, Agent, or Firm* — Fish & Richardson P.C.

(57) ABSTRACT

In an implementation, one or more user interactions from a virtual reality (VR) device user for initiating a service in a VR scenario of a VR application are detected. One or more eye physiological characteristics of the VR device user are obtained for user identity authentication. The obtained one or more eye physiological characteristics are compared with one or more pre-stored eye physiological characteristics samples. The VR device user is authenticated if the one or more eye physiological characteristics match at least a portion of the one or more pre-stored eye physiological characteristics samples, and a server that provides and performs the service is communicated with.

20 Claims, 2 Drawing Sheets

(51) Int. Cl.
| | |
|---|---|
| *G06V 40/19* | (2022.01) |
| *A61B 3/00* | (2006.01) |
| *A61B 3/14* | (2006.01) |
| *G06T 19/00* | (2011.01) |
| *H04N 5/225* | (2006.01) |
| *H04N 5/33* | (2006.01) |
| *G06V 40/10* | (2022.01) |

(52) U.S. Cl.
CPC .............. *A61B 3/14* (2013.01); *G06T 19/006* (2013.01); *G06V 40/19* (2022.01); *H04N 5/2256* (2013.01); *H04N 5/33* (2013.01); *G06V 40/15* (2022.01)

(58) Field of Classification Search
CPC ....... H04N 21/25875; H04N 21/42201; G06K 9/00617; G06K 9/00671; A61B 3/0008; A61B 3/14; A61B 3/25; H04L 63/0861
See application file for complete search history.

(56) References Cited

U.S. PATENT DOCUMENTS

| | | | |
|---|---|---|---|
| 8,411,909 B1* | 4/2013 | Zhao | G06K 9/00899 382/116 |
| 9,274,599 B1* | 3/2016 | D'Amico | G06F 3/013 |
| 9,360,682 B1* | 6/2016 | Edwards | G02C 11/10 |
| 9,392,324 B1* | 7/2016 | Maltar | H04N 21/47214 |
| 9,576,285 B2 | 2/2017 | Zhou | |
| 9,785,250 B1* | 10/2017 | Staton | G06F 3/0304 |
| 10,039,445 B1* | 8/2018 | Torch | G06K 9/0061 |
| 2003/0091215 A1 | 5/2003 | Lauper et al. | |
| 2005/0102502 A1* | 5/2005 | Sagen | H04L 63/0823 713/156 |
| 2008/0037835 A1* | 2/2008 | Lee | G06K 9/00604 382/117 |
| 2010/0074477 A1 | 3/2010 | Fujii et al. | |
| 2011/0213664 A1 | 9/2011 | Osterhout et al. | |
| 2011/0227741 A1 | 9/2011 | Jeon | |
| 2012/0066757 A1 | 3/2012 | Vysogorets et al. | |
| 2012/0154277 A1 | 6/2012 | Bar-Zeev et al. | |
| 2013/0005443 A1 | 1/2013 | Kosta et al. | |
| 2013/0044130 A1 | 2/2013 | Geisner et al. | |
| 2013/0114850 A1 | 5/2013 | Publicover et al. | |
| 2013/0169683 A1 | 7/2013 | Perez et al. | |
| 2013/0197968 A1* | 8/2013 | Davis | H04L 67/306 705/7.29 |
| 2013/0232430 A1 | 9/2013 | Reitan | |
| 2014/0055591 A1 | 2/2014 | Katz | |
| 2014/0055746 A1 | 2/2014 | Nistico et al. | |
| 2014/0125574 A1 | 5/2014 | Scavezze et al. | |
| 2014/0197922 A1 | 7/2014 | Stanwood et al. | |
| 2014/0226000 A1* | 8/2014 | Vilcovsky | G06F 3/017 348/77 |
| 2015/0139509 A1 | 5/2015 | Yang | |
| 2015/0201835 A1 | 7/2015 | Border et al. | |
| 2015/0205348 A1 | 7/2015 | Nortrup et al. | |
| 2015/0241965 A1 | 8/2015 | Nortrup et al. | |
| 2015/0260986 A1 | 9/2015 | Nortrup et al. | |
| 2015/0309705 A1 | 10/2015 | Keeler et al. | |
| 2015/0326570 A1 | 11/2015 | Publicover et al. | |
| 2016/0014121 A1* | 1/2016 | Perna | G06K 9/2027 726/4 |
| 2016/0018645 A1 | 1/2016 | Haddick et al. | |
| 2016/0019423 A1* | 1/2016 | Ortiz | G06K 9/00885 345/633 |
| 2016/0026253 A1 | 1/2016 | Bradski et al. | |
| 2016/0063767 A1 | 3/2016 | Lee et al. | |
| 2016/0116979 A1 | 4/2016 | Border | |
| 2016/0124501 A1 | 5/2016 | Lam et al. | |
| 2016/0225164 A1 | 8/2016 | Tomlin et al. | |
| 2016/0246367 A1 | 8/2016 | Tungare et al. | |
| 2016/0260206 A1 | 9/2016 | Jung et al. | |
| 2016/0260258 A1 | 9/2016 | Lo et al. | |
| 2016/0267716 A1 | 9/2016 | Patel | |
| 2016/0300388 A1* | 10/2016 | Stafford | A63F 13/69 |
| 2016/0307038 A1* | 10/2016 | Skogo | G06K 9/00604 |
| 2016/0335495 A1 | 11/2016 | Kim et al. | |
| 2016/0342782 A1* | 11/2016 | Mullins | G06F 21/32 |
| 2016/0343168 A1 | 11/2016 | Mullins et al. | |
| 2016/0371555 A1* | 12/2016 | Derakhshani | A61B 5/1102 |
| 2017/0011263 A1* | 1/2017 | Andersen | G06F 21/32 |
| 2017/0358141 A1* | 12/2017 | Stafford | G06F 3/011 |
| 2018/0029319 A1 | 2/2018 | Kalima et al. | |
| 2018/0121724 A1* | 5/2018 | Ovsiannikov | G06K 9/00033 |
| 2018/0150690 A1 | 5/2018 | Yin | |
| 2018/0253897 A1 | 9/2018 | Satake | |
| 2018/0323972 A1 | 11/2018 | Reed et al. | |
| 2019/0236390 A1* | 8/2019 | Guo | G06K 9/00892 |
| 2019/0260981 A1 | 8/2019 | Ollila | |
| 2019/0332758 A1 | 10/2019 | Yin et al. | |

FOREIGN PATENT DOCUMENTS

| | | |
|---|---|---|
| CN | 103870738 | 6/2014 |
| CN | 105183147 | 12/2015 |
| CN | 105427107 | 3/2016 |
| CN | 105635093 | 6/2016 |
| CN | 105825107 | 8/2016 |
| CN | 105912110 | 8/2016 |
| CN | 105955491 | 9/2016 |
| CN | 106022036 | 10/2016 |
| CN | 106156578 | 11/2016 |
| CN | 106203372 | 12/2016 |
| CN | 106203410 | 12/2016 |
| CN | 107122642 | 9/2017 |
| EP | 2410490 | 1/2012 |
| GB | 2317528 | 3/1998 |
| GN | 105930816 | 9/2016 |
| JP | 200330469 | 1/2003 |
| JP | 2004261515 | 9/2004 |
| JP | 2004337348 | 12/2004 |
| JP | 2009150866 | 7/2009 |
| JP | 2009199392 | 9/2009 |
| JP | 2014092940 | 5/2014 |
| JP | 2015012304 | 1/2015 |
| KR | 20130107981 | 10/2013 |
| KR | 20150112621 | 10/2015 |
| KR | 20160056589 | 5/2016 |
| KR | 101645087 | 8/2016 |
| TW | 200701104 | 1/2007 |
| TW | M514608 | 12/2015 |
| TW | 201631534 | 9/2016 |
| WO | WO 20091107704 | 9/2009 |
| WO | WO 2016010721 | 1/2016 |
| WO | WO 2016018488 | 2/2016 |
| WO | WO 2016058528 | 4/2016 |
| WO | WO 2016168814 | 10/2016 |
| WO | 2016/183541 | 11/2016 |
| WO | WO 2016183020 | 11/2016 |

OTHER PUBLICATIONS

Nakamoto, "Bitcoin: A Peer-to-Peer Electronic Cash System," www.bitcoin.org, 2005, 9 pages.
International Search Report and Written Opinion of the International Searching Authority issued in International Appiication No. PCT/US2017/063226 dated Feb. 14, 2018; 7 pages.
International Search Report and Written Opinion of the International Searching Authority issued in International Application No. PCT/US2017/063223 dated Feb. 9, 2018; 7 pages.
International Preliminary Report on Patentability in International Application No. PCT/US2017/063223, dated Jan. 15, 2019, 17 pages.
International Preliminary Report on Patentability in International Application No. PCT/US2017/063226, dated Jan. 24, 2019, 24 pages.
Extended European Search Report in European Application No. 17875636.7, dated Oct. 28, 2019, 8 pages.
Extended European Search Report in European Application No. 17877053.3, dated Dec. 2, 2019, 9 pages.

(56) References Cited

OTHER PUBLICATIONS

U.S. Appl. No. 16/507,944, filed Jul. 10, 2019, Yin et al.
Extended European Search Report in European Application No. 18768201.8, dated Oct. 2, 2019, 13 pages.
PCT International Preliminary Report on Patentability in International Application No. PCT/CN2018/078904, dated Sep. 17, 2019, 9 pages (with English translation).
PCT International Search Report and Written Opinion in International Application No. PCT/CN2018/078904, dated Jun. 13, 2018, 10 pages (with partial English translation).
Bhardwaj et al., "Liveness Detection Using Eye Blink A Case Study," International Journal of Application or Innovation in Engineering & Management (IJAIEM), Nov. 2012, 1(3):21-28.
Pan et al., "Eyeblink-based Anti-Spoofing in Face Recognition from a Generic Webcamera," 2007 IEEE 11th International Conference on Computer Vision, Jan. 2007, 8 pages.
Changxin High Technology—Computer Technology, Xu et al. (ed)., Nov. 1998, p. 69 (with English machine translation).
Digital Media Technology, Ding et al. (ed)., Aug. 2015, p. 209 (with English machine translation).
Virtual Reality Technology, Shen et al. (ed)., Sep. 2002, pp. 47-48 (with English machine translation).

* cited by examiner

SERVICE CONTROL AND USER IDENTITY AUTHENTICATION BASED ON VIRTUAL REALITY

The application claims priority to Chinese Patent Application No. 201611079020.8, filed on Nov. 29, 2016, which is incorporated by reference in its entirety. The subject matter of the present invention is also related to U.S. patent application Ser. No. 15/819,034, filed on Nov. 21, 2017, which is incorporated by reference in its entirety.

TECHNICAL FIELD

This disclosure relates to virtual reality applications, and more particularly to service control and user identity authentication based on virtual reality.

BACKGROUND

Virtual reality (VR) is a computer technology that uses VR devices, such as headsets, sometimes in combination with physical spaces or multi-projected environments, to generate realistic images, sounds, and other sensations that simulate a user's physical presence in a three dimensional (3D) virtual environment and allows the VR user to interact with the virtual environment. Many applications, such as those for gaming, content consumption, and productivity, have been developed to provide user an immersive experience using VR technology. Many VR applications allow in-application purchases, user customization, or parental control. These operations should require user identity authentication for security purposes.

SUMMARY

The present disclosure describes methods and systems, including computer-implemented methods, computer program products, and computer systems for service control and user identity authentication based on virtual reality (VR).

In an implementation, one or more user interactions from a VR device user for initiating a service in a VR scenario of a VR application are detected. One or more eye physiological characteristics of the VR device user are obtained for user identity authentication. The obtained one or more eye physiological characteristics are compared with one or more pre-stored eye physiological characteristics samples. The VR device user is authenticated if the one or more eye physiological characteristics match at least a portion of the one or more pre-stored eye physiological characteristics samples, and a server that provides and performs the service is communicated with.

Implementations of the described subject matter, including the previously described implementation, can be implemented using a computer-implemented method; a non-transitory, computer-readable medium storing computer-readable instructions to perform the computer-implemented method; and a computer-implemented system comprising one or more computer memory devices interoperably coupled with one or more computers and having tangible, non-transitory, machine-readable media storing instructions that, when executed by the one or more computers, perform the computer-implemented method/the computer-readable instructions stored on the non-transitory, computer-readable medium.

The subject matter described in this specification can be implemented in particular implementations, so as to realize efficient user identity authentication in a virtual environment to provide faster, more convenient operations, and more immersive experience to VR users.

The details of one or more implementations of the subject matter of this specification are set forth in the Detailed Description, the Claims, and the accompanying drawings. Other features, aspects, and advantages of the subject matter will become apparent to those of ordinary skill in the art from the Detailed Description, the Claims, and the accompanying drawings.

DESCRIPTION OF DRAWINGS

Like reference numbers and designations in the various drawings indicate like elements.

DETAILED DESCRIPTION

The following detailed description describes technologies related to performing biometric authentication based on a virtual reality (VR) device user's eye physiological characteristics, and is presented to enable any person skilled in the art to make and use the disclosed subject matter in the context of one or more particular implementations. Various modifications, alterations, and permutations of the disclosed implementations can be made and will be readily apparent to those or ordinary skill in the art, and the general principles defined can be applied to other implementations and applications, without departing from the scope of the present disclosure. In some instances, one or more technical details that are unnecessary to obtain an understanding of the described subject matter and that are within the skill of one of ordinary skill in the art may be omitted so as to not obscure one or more described implementations. The present disclosure is not intended to be limited to the described or illustrated implementations, but to be accorded the widest scope consistent with the described principles and features.

VR is a computer technology that uses VR devices, such as headsets, sometimes in combination with physical spaces or multi-projected environments, to generate realistic images, sounds, and other sensations that simulate a user's physical presence in a three-dimensional (3D) virtual environment and allows the VR user to interact with the virtual environment. Many applications, such as those for gaming, content consumption, and productivity, have been developed to provide user an immersive experience using VR technology. Many VR applications allow in-application purchases, user customization, or parental control. These operations should require user identity authentication for security purposes.

The present disclosure describes technologies for faster and more convenient user identity authentication based on a VR device user's eye physiological characteristics. When a user uses a VR device to perform a service, the VR device can identify user interaction operations with virtual elements rendered in the virtual reality scenario using one or more sensors. When it is identified that the user interaction operations match one or more pre-stored operations, the VR device can invoke biometric authentication based on the user's eye physiological characteristics for user identity verification. If the biometric authentication is successful, the user can perform a service interaction to complete the service. As such, the VR device can collect a user's eye physiological characteristics to quickly perform biometric authentication in the VR environment, to simplify the user identity authentication procedure and ensure account security. For example, when using a payment service in a VR environment, biometric authentication through the VR device can allow faster user identity authentication, as compared to entering a password through complicated user interactions with a virtual keyboard.

Figure 1:
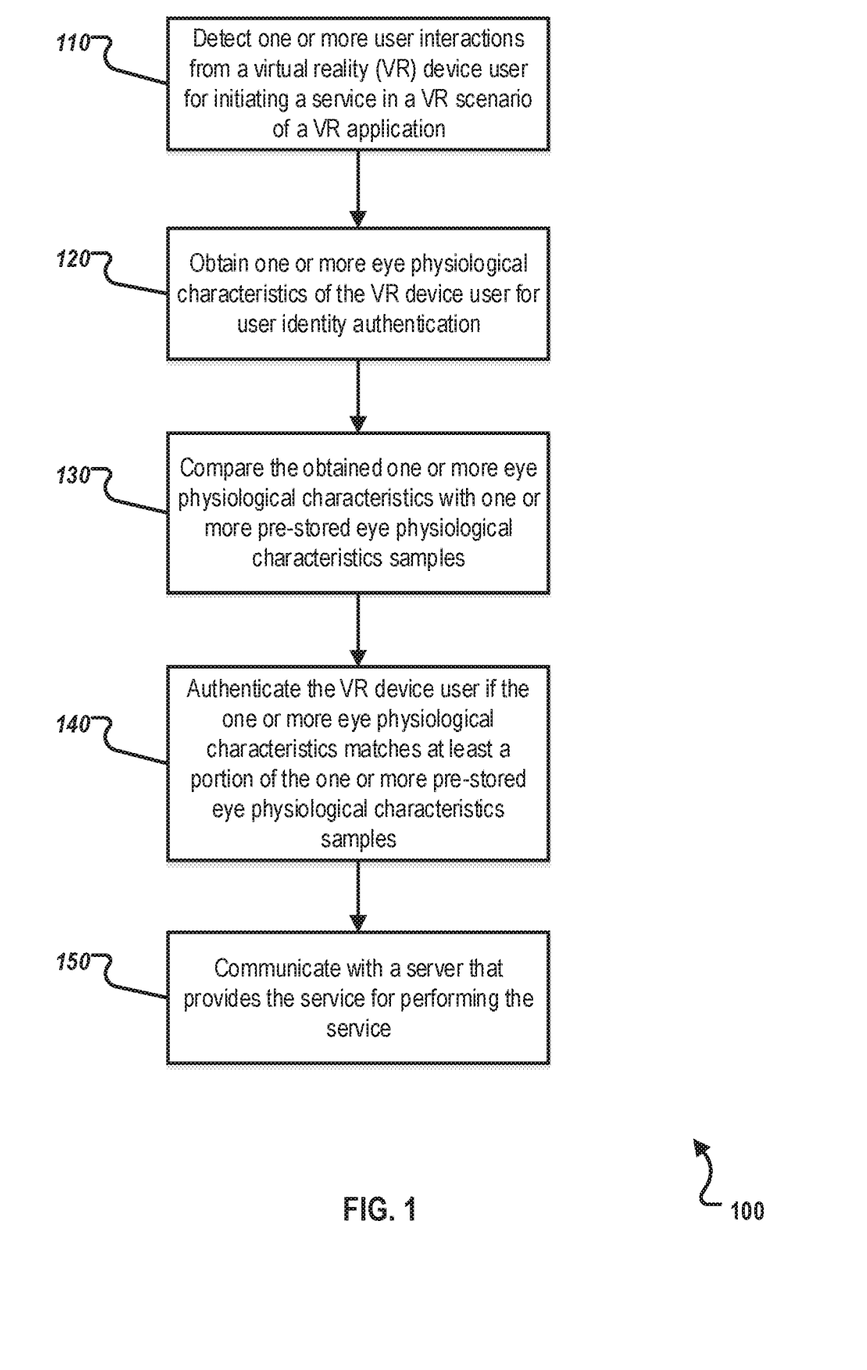
FIG. 1 is a flowchart illustrating an example of a method for performing user identity authentication based on eye physiological characteristics in a virtual reality scenario, according to an implementation of the present disclosure.

FIG. 1 is a flowchart illustrating an example method for performing user identity authentication based on eye physiological characteristics in a virtual reality scenario, according to an implementation of the present disclosure. For clarity of presentation, the description that follows generally describes method 100 in the context of the other figures in this description. However, it will be understood that method 100 can be performed, for example, by any suitable system, environment, software, and hardware, or a combination of systems, environments, software, and hardware, as appropriate. In some implementations, various steps of method 100 can be run in parallel, in combination, in loops, or in any order. The VR software can be developed to provide a 3D immersive VR user experience.

At 110, one or more user interactions from a VR device user for initiating a service in a VR scenario of a VR application are detected. The service can be any service or task offered in a VR application performed by the user that requires user identity authentication. In some cases, the service can be a local task performed by a user computing device or an online task performed by a server. For example, the service can be an online payment service, such as payment made in VR applications such as VR shopping, VR games, VR based video-on-demand, or donation to a VR live cast. Alternatively, the service can be a local service that requires user account login or password protected unlock. The VR application can be any software or application that is developed based on VR. The VR application can render a VR scenario through the VR device to provide user with immersive 3D experience.

The VR scenario or VR environment can be created by VR modeling using a modeling tool, such as UNITY, 3DSMAX, or PHOTOSHOP. In some cases, the VR modeling and VR scenario texture mapping can be based on real life scenarios. For example, texture maps of materials and real life scenario models can first be collected by photographing real life objects or scenarios. Modeling tools such as PHOTOSHOP or 3DMAX can then be used for texture processing and real-life 3D model creation. The 3D model can then be imported to a UNITY3D (U3D) platform and multi-dimensionally rendered through sound effects, graphical interfaces, plug-ins, and lighting. Interaction code can then be executed to convert the 3D model to the VR scenario model.

After the VR scenario and service interface modeling, the VR device can present the VR scenario and the service interface to the user. In some cases, the VR scenario model and a virtual element for triggering the service interface can be presented to the user. When a user needs to perform the service while having an immersive experience in the VR scenario, the user can interact with the virtual element to trigger the service interface.

The user can interact with the virtual element through any movements or gestures, such as a head movement and hand gesture. For example, the user can move their head to control the movement of their visual focus, which can be used as the operation focus (for example, a cursor) in the VR scenario. The VR device can use a sensor to track the movement of the head, and use the sensed movement to change the operational focus in the VR scenario. When the user moves their head to change the operation focus to a virtual element and stay focused on the virtual element for a predetermined amount of time (for example, three seconds), the VR device can determine that the virtual element is selected and trigger the service interface in the VR scenario.

As another example, the user can position the operation focus on the virtual element by moving their hand, and then using a predetermined 3D gesture to select the virtual element. The VR device can use a sensor to track the user's hand movement, calculate depth information of the user's hand with respect to the VR scenario based on the user's hand displacement sensed by the sensor, and then restore a 3D gesture made by the user in the VR scenario. If the 3D gesture is the same as one of the pre-stored gestures, the VR device can select the virtual element and trigger the service interface in the VR scenario.

In some cases, the one or more user interactions can include a voice command. The VR device can use voice recognition software to recognize a user's voice command. As such, when the user needs to perform a service while having an immersive experience in the VR scenario, the user can use voice command to initiate the service instead of interacting with one or more virtual elements to trigger the service interface.

In some cases, the VR device can collect the voice input from the VR user and use the voice recognition software to recognize voice commands dictated by the user. In some other cases, voice recognition can be performed by a server that provides the service. For example, a service platform formed by a server cluster can designate a server for voice recognition service and provide an access interface for the VR device to access the voice recognition service. After collecting the voice input from the user, the VR device can construct a voice recognition request based on the collected voice input, and send the voice recognition request through the access interface to the server.

After receiving the voice recognition request, the server can parse the voice recognition request, identify the voice command, and recognize the voice command using a voice recognition algorithm. After recognizing the voice command, the server can convert the voice command to a character string instruction recognizable by the VR device, and send the character string instruction to the VR device. After receiving the character string instruction, the VR device can determine whether the character string instruction is an executable instruction corresponding to the service. If yes, the VR device can initiate the service in response to the instruction.

For example, when the service is a payment service based on a VR application, the user can send a voice command of "start to pay." After performing voice recognition, the server can convert the voice command into a character string instruction recognizable by the VR device, and the VR device can initiate the payment process in response to the instruction.

In addition to using voice command to initiate services, voice commands can be used to perform other voice controls, such as cancellation of a service, as long as those control functions are available to the service. When the cancellation voice command is successfully recognized and converted into a character string instruction, the VR device can respond to the cancellation instruction and cancel the service. For example, when the service is a payment service based on a VR application, the user can cancel the payment service after the service being initiated by the voice command "start to pay." The user can dictate a voice command "cancel payment." After the voice command "cancel payment" is recognized by the server and converted to a character string instruction, the VR device can respond to the instruction and terminate the payment process.

The VR device user can also use voice command to control how the service is performed. Using again the payment service based on a VR application for example, a user can switch the payment method from debit card to credit card by dictating "switch to credit card," and sending the additional voice command "please pay by credit card" to perform the credit card payment. From 110, method 100 proceeds to 120.

At 120, one or more eye physiological characteristics of the VR device user are obtained for user identity authentication. After a service is initiated, the VR device can present a UI in a virtual scenario for user identity authentication. In some cases, the VR device can include eye recognition function to facilitate user identity authentication. The eye recognition function can be performed based on eye physiological characteristics sampling algorithm. The eye physiological characteristics sampling algorithm can use one or more of the user's eye physiological characteristics gathered by an eye sensor to verify the user's identity. Example eye physiological characteristics can include eye print and iris characteristics. The eye physiological characteristics sampling algorithm can include an eye print sampling algorithm and iris sampling algorithm.

The eye sensor can be built-in to the VR device, separate from, but communicably coupled to, the VR device, or integrated on a mobile device such as a smartphone. In some cases, the VR device can be a slide-in type VR headset, which can function by inserting or sliding in a smartphone that can communicate with the headset, and convert the images displayed on the cell phone to VR scenarios. In such cases, the VR device can rely on the built-in eye sensor to perform eye recognition.

The eye sensor can include an optical lens, installed relative to the positions of the VR device user's eyes, and one or more cameras distributed around the optical lens. In some cases, the cameras can be uniformly distributed around the lens. The cameras can be positioned on an external surface of the lens, or in other suitable places, to ensure that the lens is located between the user's eyes and the cameras.

In some cases, the physiological characteristic of the eye is the user's iris. The user's iris can be imaged under an infrared light source. The cameras distributed around the lenses can then be infrared cameras. In some cases, the physiological characteristic of the eye is an eye print of the user, in such cases, the cameras can be RGB cameras.

In some cases, when invoking the eye sensor to collect the eye physiological characteristics, the VR device can be affected by the internal ambient light of the VR device. The eye sensor can further include one or more LED light sources that have a one-to-one correspondence with the one or more cameras uniformly distributed around the lenses. In some cases, when the iris is used as the physiological characteristic of the eye, the LED light source can be an infrared LED light source.

The VR device can also include a light sensor to detect the brightness of the ambient light inside the VR device. If the brightness is lower than a predetermined value that can affect the imaging of eye physiological characteristics, the VR device can turn one or more of the LED light sources on, to perform one-to-one light compensation to the one or more cameras, to compensate for relatively poor light condition inside the VR device.

In some cases, the physical dimension of the VR device can cause insufficient depth of field between the cameras and the user's eyes, such that the cameras cannot be accurately focused on the iris or eye print. In such cases, one or more macro lens cameras can be used. Alternatively, to adaptively adjust the focal length, one or more additional, optical lenses can be installed at a position between the user's eyes and the lens to reflect or refract light rays coming from the user's eyes, based on the internal shape of the VR device (for example, the cavity of a VR headset). In some cases, special lenses, such as an endoscope, can be used to collect the user's iris or eye print features. In some cases, a user can manually adjust the focal length of the cameras to obtain accurate iris or eye print images. From 120, method 100 proceeds to 130.

At 130, the obtained one or more eye physiological characteristics are compared with one or more pre-stored eye physiological characteristics samples. In some cases, the user can use the VR device to obtain one or more eye physiological characteristics samples during service account registration. The one or more eye physiological characteristics samples can be saved locally for applications that allow offline biometric authentication or included in an authentication request to be sent to a service server for online authentication. For example, when the service is a VR payment service, the service account of the user can be a payment account. The VR device can use an integrated eye sensor to obtain the user's eye physiological characteristics sample during payment account registration and save the sample locally, or on the payment server. The eye physiological characteristics sample is associated with the user's payment account.

In some cases, the user can log into the user account to use the VR device. The VR device can send the eye physiological characteristics sample and VR device user account login information as a registration message to the service server. The server can use the received information to associate the user's eye physiological characteristics sample to its service account and save the eye physiological characteristics sample to a biometric characteristics database. In some cases, the user account can be the same as the service account.

In some cases, after eye physiological characteristics is collected by the VR device, the VR device can generate a biometric recognition request to the service server. The biometric recognition request can include the user's user or service account information and eye physiological characteristics obtained by the eye sensor. The service server can provide a biometric recognition interface to the VR device for receiving the request and submit the request to the server. In some cases, the service server can cooperate with a biometric recognition server and the biometric recognition interface can be provided by the biometric recognition server. From 130, method 100 proceeds to 140.

At 140, the VR device user is authenticated if the one or more eye physiological characteristics match at least a portion of the one or more pre-stored eye physiological characteristics samples. After receiving the biometric recognition request, the service server can parse the request, acquire the eye physiological characteristics and the user account information, and compare the eye physiological characteristics with eye physiological characteristics samples stored in a biometric characteristic database. In some cases, if the eye physiological characteristics match at least a portion of the eye physiological characteristics samples, the service server can further verify whether the received user account information matches the account associated with the matching biometric sample. After comparing the biometric information and user account information with the corresponding information stored in the biometric characteristic database, the service server can return an authentication result to the VR device. The authentication result can be returned as a Boolean-type return value (that is, false or true). If one or both the biometric information and user account information match the corresponding information stored in the biometric characteristic database, a "true" value can be returned to indicate that the biometric authentication succeeded. Otherwise, a "false" value can be returned to indicate that the biometric authentication failed.

In some cases, the VR device can perform biometric authentication locally. The user's eye physiological characteristics can be saved in the VR device during biometric information registration (for example, registering eye print information to the user account on the VR device). After the user initiates the service in the VR scenario, the VR device can collect the eye physiological characteristics of the user, and compare the eye physiological characteristics with the eye physiological characteristics samples saved during biometric information registration. If the eye physiological characteristics match at least a portion of the saved information, the biometric authentication for the service succeeds. Otherwise, the biometric authentication fails.

In some cases, the VR device can perform additional biometric authentication before sending the registration message to the service server for enhanced security. For example, the VR device can prompt the user to input a password or other security information to verify the user's identity before sending the user's registration message to the service server. This process can prevent unauthorized users from fraudulently registering their biometric information to bind with the authorized user's user account. After service registration, the VR device can initiate biometric authentication based on the user's eye physiological characteristics sample, after the user initiates the service.

In some cases, the VR device can perform a bioassay process, before collecting biometric information, to ensure that the VR device is currently used by a real person. This process can prevent unauthorized users from using eye print or iris images of the authorized user for biometrical authentication and illegally accessing the authorized user's service account. Example bioassay processes can include eye-blinking or heartbeat recognition.

After a real user is detected using the bioassay process, the VR device can prompt the user to perform biometric authentication for accessing the service account. Using again a VR payment service for example, the VR device can present a text prompt in the VR scenario such as "Please scan your iris for payment authentication." After 140, method 100 proceeds to 150.

At 150, a server is communicated with to perform the service. If the biometric authentication is successful (for example, a returned value is "true"), the VR device can present the service interface corresponding to the service to gather data related to the service, establish a service request, submit the service request to the service server through a service access interface, and perform further interactions with the service server, if needed, to perform the service.

Using again the VR payment service for example, the VR device can present a payment interface to gather payment related data, such as user name, order information, and price, and then generate a payment processing request and send the payment processing request to the service server. The service server can process the request and complete the payment.

The following example uses VR shopping to illustrate how biometric authentication based on eye physiological characteristics can provide safer, faster, and simpler service experience to the user. It is assumed that the physiological characteristic of the eye used is the eye print. The service for the VR shopping can be a payment service such as ALIPAY. The virtual element can be a virtual button presented in the VR shopping scenario. The server for the payment service can be a payment server such as the ALIPAY platform based on a server cluster.

The user can first log in to the VR device using the user account or payment account, and complete eye print registration on the VR device to associate the user's eye print to the payment account. The user's account information and corresponding eye print information can be stored in a biometric characteristic database on a payment server. After eye print registration, the user can use their finger for biometric authentication in a VR environment.

When wearing the VR device for VR shopping, the items for sale can be presented to the user in the VR scenario and the user can flip through the item list, select items, or add items to the shopping cart using gestures or head movements. In some cases, a virtual button (that is, the virtual element) for checkout or pay can be provided when an item is selected or added to the user's shopping cart. The user can, again, use gesture or head movements to move the operation focus (for example, a cursor) to the virtual button and use a predetermined gesture or head movement to select the virtual button.

The payment service can be initiated after the service is initiated by the user's voice command. In some cases, The VR device can perform a bioassay process to determine whether a real user of the VR device is present. If so, the VR device can prompt a message "Please keep your eyes open for payment authentication" in the VR scenario.

After the eye physiological characteristics are collected, the VR device can send a biometric authentication request including the collected eye print information and the user's user or payment account information to the payment server. The payment server can compare the eye print information with the eye print information stored in the biometric characteristic database during eye print registration. If the received eye print information matches the eye print associated with the user account stored in the database, and the payment account information is consistent with the stored user account information, the payment server can return a Boolean-type "true" value to the VR device to indicate that the eye print authentication is successful.

After having acknowledged that the payment was successful, the VR device can present a payment interface for the user to input payment data, such as user name, order information, and payment amount related to the payment service, and generate and send a payment processing request to the payment server. The payment server can process the payment and complete the purchase.

In some cases, an "authentication-free for small amount" payment process can be used to further facilitate payment speed. For example, when the user initiates the payment service using voice command, the VR device can check the price of the items and determine whether the payment amount is less than a preset amount (for example, 20USD). If the payment amount is less than the preset amount, the VR device can directly generate and send the payment processing request to the payment server without biometric authentication. Otherwise, the user may need to perform biometric authentication before the payment service can be used. After 130, method 100 ends.

Figure 2:
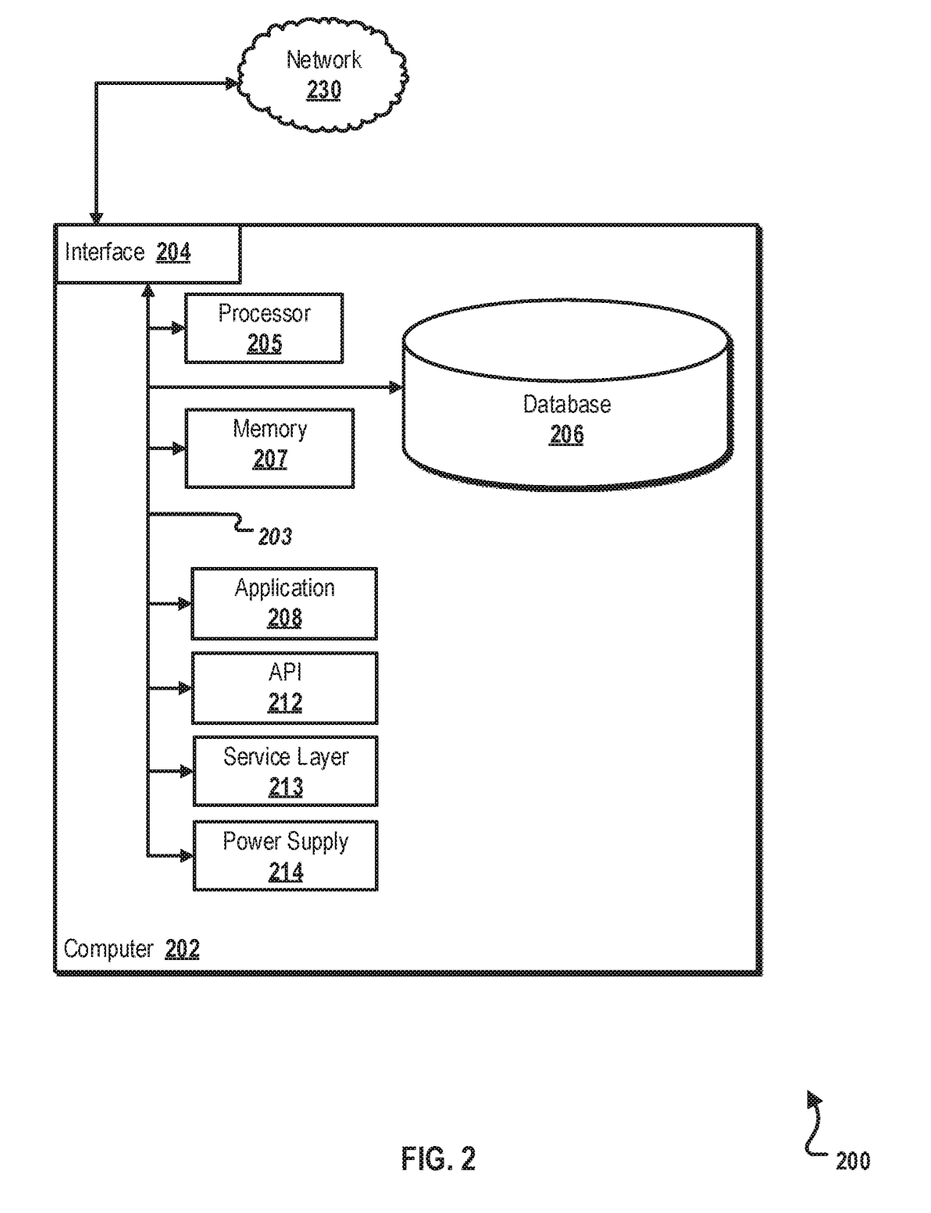
FIG. 2 is a block diagram illustrating an example of a computer-implemented system used to provide computational functionalities associated with described algorithms, methods, functions, processes, flows, and procedures, according to an implementation of the present disclosure.

FIG. 2 is a block diagram illustrating an example of a computer-implemented System 200 used to provide computational functionalities associated with described algorithms, methods, functions, processes, flows, and procedures, according to an implementation of the present disclosure. In the illustrated implementation, System 200 includes a Computer 202 and a Network 230.

The illustrated Computer 202 is intended to encompass any computing device such as a server, desktop computer, laptop/notebook computer, wireless data port, smart phone, personal data assistant (PDA), tablet computer, one or more processors within these devices, another computing device, or a combination of computing devices, including physical or virtual instances of the computing device, or a combination of physical or virtual instances of the computing device. Additionally, the Computer 202 can include an input device, such as a keypad, keyboard, touch screen, another input device, or a combination of input devices that can accept user information, and an output device that conveys information associated with the operation of the Computer 202, including digital data, visual, audio, another type of information, or a combination of types of information, on a graphical-type user interface (UI) (or GUI) or other UI.

The Computer 202 can serve in a role in a distributed computing system as a client, network component, a server, a database or another persistency, another role, or a combination of roles for performing the subject matter described in the present disclosure. The illustrated Computer 202 is communicably coupled with a Network 230. In some implementations, one or more components of the Computer 202 can be configured to operate within an environment, including cloud-computing-based, local, global, another environment, or a combination of environments.

At a high level, the Computer 202 is an electronic computing device operable to receive, transmit, process, store, or manage data and information associated with the described subject matter. According to some implementations, the Computer 202 can also include or be communicably coupled with a server, including an application server, e-mail server, web server, caching server, streaming data server, another server, or a combination of servers.

The Computer 202 can receive requests over Network 230 (for example, from a client software application executing on another Computer 202) and respond to the received requests by processing the received requests using a software application or a combination of software applications. In addition, requests can also be sent to the Computer 202 from internal users (for example, from a command console or by another internal access method), external or third-parties, or other entities, individuals, systems, or computers.

Each of the components of the Computer 202 can communicate using a System Bus 203. In some implementations, any or all of the components of the Computer 202, including hardware, software, or a combination of hardware and software, can interface over the System Bus 203 using an application programming interface (API) 212, a Service Layer 213, or a combination of the API 212 and Service Layer 213. The API 212 can include specifications for routines, data structures, and object classes. The API 212 can be either computer-language independent or dependent and refer to a complete interface, a single function, or even a set of APIs. The Service Layer 213 provides software services to the Computer 202 or other components (whether illustrated or not) that are communicably coupled to the Computer 202. The functionality of the Computer 202 can be accessible for all service consumers using the Service Layer 213. Software services, such as those provided by the Service Layer 213, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the Computer 202, alternative implementations can illustrate the API 212 or the Service Layer 213 as stand-alone components in relation to other components of the Computer 202 or other components (whether illustrated or not) that are communicably coupled to the Computer 202. Moreover, any or all parts of the API 212 or the Service Layer 213 can be implemented as a child or a sub-module of another software module, enterprise application, or hardware module without departing from the scope of the present disclosure.

The Computer 202 includes an Interface 204. Although illustrated as a single Interface 204, two or more Interfaces 204 can be used according to particular needs, desires, or particular implementations of the Computer 202. The Interface 204 is used by the Computer 202 for communicating with another computing system (whether illustrated or not) that is communicatively linked to the Network 230 in a distributed environment. Generally, the Interface 204 is operable to communicate with the Network 230 and includes logic encoded in software, hardware, or a combination of software and hardware. More specifically, the Interface 204 can include software supporting one or more communication protocols associated with communications such that the Network 230 or hardware of Interface 204 is operable to communicate physical signals within and outside of the illustrated Computer 202.

The Computer 202 includes a Processor 205. Although illustrated as a single Processor 205, two or more Processors 205 can be used according to particular needs, desires, or particular implementations of the Computer 202. Generally, the Processor 205 executes instructions and manipulates data to perform the operations of the Computer 202 and any algorithms, methods, functions, processes, flows, and procedures as described in the present disclosure.

The Computer 202 also includes a Database 206 that can hold data for the Computer 202, another component communicatively linked to the Network 230 (whether illustrated or not), or a combination of the Computer 202 and another component. For example, Database 206 can be an in-memory, conventional, or another type of database storing data consistent with the present disclosure. In some implementations, Database 206 can be a combination of two or more different database types (for example, a hybrid in-memory and conventional database) according to particular needs, desires, or particular implementations of the Computer 202 and the described functionality. Although illustrated as a single Database 206, two or more databases of similar or differing types can be used according to particular needs, desires, or particular implementations of the Computer 202 and the described functionality. While Database 206 is illustrated as an integral component of the Computer 202, in alternative implementations, Database 206 can be external to the Computer 202.

The Computer 202 also includes a Memory 207 that can hold data for the Computer 202, another component or components communicatively linked to the Network 230 (whether illustrated or not), or a combination of the Computer 202 and another component. Memory 207 can store any data consistent with the present disclosure. In some implementations, Memory 207 can be a combination of two or more different types of memory (for example, a combination of semiconductor and magnetic storage) according to particular needs, desires, or particular implementations of the Computer 202 and the described functionality. Although illustrated as a single Memory 207, two or more Memories 207 or similar or differing types can be used according to particular needs, desires, or particular implementations of the Computer 202 and the described functionality. While Memory 207 is illustrated as an integral component of the Computer 202, in alternative implementations, Memory 207 can be external to the Computer 202.

The Application 208 is an algorithmic software engine providing functionality according to particular needs, desires, or particular implementations of the Computer 202, particularly with respect to functionality described in the present disclosure. For example, Application 208 can serve as one or more components, modules, or applications. Further, although illustrated as a single Application 208, the Application 208 can be implemented as multiple Applications 208 on the Computer 202. In addition, although illustrated as integral to the Computer 202, in alternative implementations, the Application 208 can be external to the Computer 202.

The Computer 202 can also include a Power Supply 214. The Power Supply 214 can include a rechargeable or non-rechargeable battery that can be configured to be either user- or non-user-replaceable. In some implementations, the Power Supply 214 can include power-conversion or management circuits (including recharging, standby, or another power management functionality). In some implementations, the Power Supply 214 can include a power plug to allow the Computer 202 to be plugged into a wall socket or another power source to, for example, power the Computer 202 or recharge a rechargeable battery.

There can be any number of Computers 202 associated with, or external to, a computer system containing Computer 202, each Computer 202 communicating over Network 230. Further, the term "client," "user," or other appropriate terminology can be used interchangeably, as appropriate, without departing from the scope of the present disclosure. Moreover, the present disclosure contemplates that many users can use one Computer 202, or that one user can use multiple computers 202.

Described implementations of the subject matter can include one or more features, alone or in combination.

For example, in a first implementation, a computer-implemented method, comprising: detecting one or more user interactions from a virtual reality (VR) device user for initiating a service in a VR scenario of a VR application; obtaining one or more eye physiological characteristics of the VR device user for user identity authentication; comparing the obtained one or more eye physiological characteristics with one or more pre-stored eye physiological characteristics samples; authenticating the VR device user if the one or more eye physiological characteristics match at least a portion of the one or more pre-stored eye physiological characteristics samples; and communicating with a server that provides and performs the service.

The foregoing and other described implementations can each, optionally, include one or more of the following features:

A first feature, combinable with any of the following features, wherein the one or more user interactions include a gesture, a body movement, or a body posture.

A second feature, combinable with any of the previous or following features, wherein the one or more user interactions include a voice command.

A third feature, combinable with any of the previous or following features, wherein the one or more eye physiological characteristics include iris characteristics or eye print characteristics.

A fourth feature, combinable with any of the previous or following features, further comprising: performing a bioassay process for detecting the user; and presenting a notification in the VR scenario to notify the user to perform biometric authentication if the user is detected based on the bioassay process.

A fifth feature, combinable with any of the previous or following features, wherein the bioassay process includes eye-blinking recognition or heartbeat recognition.

A sixth feature, combinable with any of the previous or following features, further comprising presenting virtual guidance in the VR scenario to obtain the one or more eye physiological characteristics.

A seventh feature, combinable with any of the previous or following features, wherein the one or more eye physiological characteristics are obtained by an eye sensor and wherein the eye sensor includes a lens and one or more cameras.

An eighth feature, combinable with any of the previous or following features, wherein the lens is a macro lens.

A ninth feature, combinable with any of the previous or following features, wherein the one or more cameras are infrared cameras.

A tenth feature, combinable with any of the previous or following features, wherein the one or more cameras are paired with one or more LED lights.

In a second implementation, a non-transitory, computer-readable medium storing one or more instructions executable by a computer system to perform operations comprising: detecting one or more user interactions from a virtual reality (VR) device user for initiating a service in a VR scenario of a VR application; obtaining one or more eye physiological characteristics of the VR device user for user identity authentication; comparing the obtained one or more eye physiological characteristics with one or more pre-stored eye physiological characteristics samples; authenticating the VR device user if the one or more eye physiological characteristics match at least a portion of the one or more pre-stored eye physiological characteristics samples; and communicating with a server that provides and performs the service.

The foregoing and other described implementations can each, optionally, include one or more of the following features:

A first feature, combinable with any of the following features, wherein the one or more user interactions include a gesture, a body movement, or a body posture.

A second feature, combinable with any of the previous or following features, wherein the one or more user interactions include a voice command.

A third feature, combinable with any of the previous or following features, wherein the one or more eye physiological characteristics include iris characteristics or eye print characteristics.

A fourth feature, combinable with any of the previous or following features, further comprising: performing a bioassay process for detecting the user; and presenting a notification in the VR scenario to notify the user to perform biometric authentication if the user is detected based on the bioassay process.

A fifth feature, combinable with any of the previous or following features, wherein the bioassay process includes eye-blinking recognition or heartbeat recognition.

A sixth feature, combinable with any of the previous or following features, further comprising presenting virtual guidance in the VR scenario to obtain the one or more eye physiological characteristics.

A seventh feature, combinable with any of the previous or following features, wherein the one or more eye physiological characteristics are obtained by an eye sensor and wherein the eye sensor includes a lens and one or more cameras.

An eighth feature, combinable with any of the previous or following features, wherein the lens is a macro lens.

A ninth feature, combinable with any of the previous or following features, wherein the one or more cameras are infrared cameras.

A tenth feature, combinable with any of the previous or following features, wherein the one or more cameras are paired with one or more LED lights.

In a third implementation, a computer-implemented system, comprising: one or more computers; and one or more computer memory devices interoperably coupled with the one or more computers and having tangible, non-transitory, machine-readable media storing one or more instructions that, when executed by the one or more computers, perform one or more operations comprising: detecting one or more user interactions from a virtual reality (VR) device user for initiating a service in a VR scenario of a VR application; obtaining one or more eye physiological characteristics of the VR device user for user identity authentication; comparing the obtained one or more eye physiological characteristics with one or more pre-stored eye physiological characteristics samples; authenticating the VR device user if the one or more eye physiological characteristics match at least a portion of the one or more pre-stored eye physiological characteristics samples; and communicating with a server that provides and performs the service.

The foregoing and other described implementations can each, optionally, include one or more of the following features:

A first feature, combinable with any of the following features, wherein the one or more user interactions include a gesture, a body movement, or a body posture.

A second feature, combinable with any of the previous or following features, wherein the one or more user interactions include a voice command.

A third feature, combinable with any of the previous or following features, wherein the one or more eye physiological characteristics include iris characteristics or eye print characteristics.

A fourth feature, combinable with any of the previous or following features, further comprising: performing a bioassay process for detecting the user; and presenting a notification in the VR scenario to notify the user to perform biometric authentication if the user is detected based on the bioassay process.

A fifth feature, combinable with any of the previous or following features, wherein the bioassay process includes eye-blinking recognition or heartbeat recognition.

A sixth feature, combinable with any of the previous or following features, further comprising presenting virtual guidance in the VR scenario to obtain the one or more eye physiological characteristics.

A seventh feature, combinable with any of the previous or following features, wherein the one or more eye physiological characteristics are obtained by an eye sensor and wherein the eye sensor includes a lens and one or more cameras.

An eighth feature, combinable with any of the previous or following features, wherein the lens is a macro lens.

A ninth feature, combinable with any of the previous or following features, wherein the one or more cameras are infrared cameras.

A tenth feature, combinable with any of the previous or following features, wherein the one or more cameras are paired with one or more LED lights.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable medium for execution by, or to control the operation of, a computer or computer-implemented system. Alternatively, or additionally, the program instructions can be encoded in/on an artificially generated propagated signal, for example, a machine-generated electrical, optical, or electromagnetic signal that is generated to encode information for transmission to a receiver apparatus for execution by a computer or computer-implemented system. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or an equivalent term as understood by one of ordinary skill in the art) refer to data processing hardware and encompass all kinds of apparatus, devices, and machines for processing data, including by way of example, a programmable processor, a computer, or multiple processors or computers. The computer can also be, or further include special purpose logic circuitry, for example, a central processing unit (CPU), an FPGA (field programmable gate array), or an ASIC (application-specific integrated circuit). In some implementations, the computer or computer-implemented system or special purpose logic circuitry (or a combination of the computer or computer-implemented system and special purpose logic circuitry) can be hardware- or software-based (or a combination of both hardware- and software-based). The computer can optionally include code that creates an execution environment for computer programs, for example, code that constitutes processor firmware, a protocol stack, a database management system, an operating system, or a combination of execution environments. The present disclosure contemplates the use of a computer or computer-implemented system with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and computers can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks; and optical memory devices, for example, digital versatile/video disc (DVD), compact disc (CD)-ROM, DVD+/-R, DVD-RAM, DVD-ROM, high-definition/density (HD)-DVD, and BLU-RAY/BLU-RAY DISC (BD), and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback (such as, visual, auditory, tactile, or a combination of feedback types). Input from the user can be received in any form, including acoustic, speech, or tactile input. In addition, a computer can interact with the user by sending documents to and receiving documents from a client computing device that is used by the user (for example, by sending web pages to a web browser on a user's mobile computing device in response to requests received from the web browser).

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a number of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, Frame Relay frames, Asynchronous Transfer Mode (ATM) cells, voice, video, data, or other information between network nodes.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what can be claimed, but rather as descriptions of features that can be specific to particular implementations of particular inventions. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method, comprising:
   detecting one or more user interactions from a virtual reality (VR) device user for initiating a payment service in a VR scenario of a VR application, wherein the VR scenario includes a virtual checkout button for the payment service, and the one or more user interactions are performed on the virtual checkout button;
   in response to detecting the one or more user interactions performed on the virtual checkout button, determining that a payment amount associated with the payment service is no less than a preset amount;
   in response to determining that the payment amount associated with the payment service is no less than the preset amount:
      determining that the VR device is currently worn by a real person based on eye-blinking recognition; and
      in response to determining that the VR device is currently worn by the real person:
         invoking an eye recognition hardware to collect one or more eye physiological characteristics of the VR device user for user identity authentication, wherein the eye recognition hardware comprises a light sensor, a plurality of lenses, and a plurality of cameras, wherein the plurality of cameras are paired with a plurality of LED lights in a one-to-one correspondence, wherein the one or more eye physiological characteristics include iris characteristics, and wherein invoking the eye recognition hardware includes:
            detecting, using the light sensor, brightness of ambient light inside the VR device; and
            in response to determining that the brightness of the ambient light inside the VR device is lower than a predetermined value, turning on one or more of the plurality of LED lights;
         comparing the one or more eye physiological characteristics with one or more pre-stored eye physiological characteristics samples; and
         authenticating the VR device user if the one or more eye physiological characteristics match at least a portion of the one or more pre-stored eye physiological characteristics samples; and
   communicating with a server that provides and performs the payment service.

2. The computer-implemented method of claim 1, wherein the one or more user interactions include a gesture, a body movement, or a body posture.

3. The computer-implemented method of claim 1, wherein the one or more user interactions include a voice command.

4. The computer-implemented method of claim 1, wherein the one or more eye physiological characteristics include eye print characteristics and the iris characteristics.

5. The computer-implemented method of claim 1, further comprising:
presenting a notification in the VR scenario to notify the VR device user to perform biometric authentication.

6. The computer-implemented method of claim 1, further comprising presenting virtual guidance in the VR scenario to obtain the one or more eye physiological characteristics.

7. The computer-implemented method of claim 1, wherein one of the plurality of lenses is a macro lens.

8. The computer-implemented method of claim 1, wherein the plurality of cameras are infrared cameras.

9. The computer-implemented method of claim 1, wherein the plurality of cameras are uniformly distributed around the plurality of lenses.

10. The computer-implemented method of claim 1, wherein focal length of the plurality of cameras are manually adjustable by the VR device user.

11. A non-transitory, computer-readable medium storing one or more instructions executable by a computer system to perform operations comprising:
detecting one or more user interactions from a virtual reality (VR) device user for initiating a payment service in a VR scenario of a VR application, wherein the VR scenario includes a virtual checkout button for the payment service, and the one or more user interactions are performed on the virtual checkout button;
in response to detecting the one or more user interactions performed on the virtual checkout button, determining that a payment amount associated with the payment service is no less than a preset amount;
in response to determining that the payment amount associated with the payment service is no less than the preset amount:
determining that the VR device is currently worn by a real person based on eye-blinking recognition; and
in response to determining that the VR device is currently worn by the real person:
invoking an eye recognition hardware to collect one or more eye physiological characteristics of the VR device user for user identity authentication, wherein the eye recognition hardware comprises a light sensor, a plurality of lenses, and a plurality of cameras, wherein the plurality of cameras are paired with a plurality of LED lights in a one-to-one correspondence, wherein the one or more eye physiological characteristics include iris characteristics, and wherein invoking the eye recognition hardware includes:
detecting, using the light sensor, brightness of ambient light inside the VR device; and
in response to determining that the brightness of the ambient light inside the VR device is lower than a predetermined value, turning on one or more of the plurality of LED lights;
comparing the one or more eye physiological characteristics with one or more pre-stored eye physiological characteristics samples; and
authenticating the VR device user if the one or more eye physiological characteristics match at least a portion of the one or more pre-stored eye physiological characteristics samples; and
communicating with a server that provides and performs the payment service.

12. The non-transitory, computer-readable medium of claim 11, wherein the one or more user interactions include a gesture, a body movement, or a body posture.

13. The non-transitory, computer-readable medium of claim 11, wherein the one or more user interactions include a voice command.

14. The non-transitory, computer-readable medium of claim 11, wherein the one or more eye physiological characteristics include eye print characteristics and the iris characteristics.

15. The non-transitory, computer-readable medium of claim 11, wherein the operations further comprise:
presenting a notification in the VR scenario to notify the VR device user to perform biometric authentication.

16. A computer-implemented system, comprising:
one or more computers; and
one or more computer memory devices interoperably coupled with the one or more computers and having tangible, non-transitory, machine-readable media storing one or more instructions that, when executed by the one or more computers, perform one or more operations comprising:
detecting one or more user interactions from a virtual reality (VR) device user for initiating a payment service in a VR scenario of a VR application, wherein the VR scenario includes a virtual checkout button for the payment service, and the one or more user interactions are performed on the virtual checkout button;
in response to detecting the one or more user interactions performed on the virtual checkout button, determining that a payment amount associated with the payment service is no less than a preset amount;
in response to determining that the payment amount associated with the payment service is no less than the preset amount:
determining that the VR device is currently worn by a real person based on eye-blinking recognition; and
in response to determining that the VR device is currently worn by the real person:
invoking an eye recognition hardware to collect one or more eye physiological characteristics of the VR device user for user identity authentication, wherein the eye recognition hardware comprises a light sensor, a plurality of lenses, and a plurality of cameras, wherein the plurality of cameras are paired with a plurality of LED lights in a one-to-one correspondence, wherein the one or more eye physiological characteristics include iris characteristics, and wherein invoking the eye recognition hardware includes: detecting, using the light sensor, brightness of ambient light inside the VR device; and in response to determining that the brightness of the ambient light inside the VR device is lower than a predetermined value, turning on one or more of the plurality of LED lights;
comparing the one or more eye physiological characteristics with one or more pre-stored eye physiological characteristics samples; and
authenticating the VR device user if the one or more eye physiological characteristics match at least a portion of the one or more pre-stored eye physiological characteristics samples; and communicating with a server that provides and performs the payment service.

17. The computer-implemented system of claim 16, wherein the one or more user interactions include a voice command.

18. The computer-implemented system of claim 16, wherein the one or more eye physiological characteristics include eye print characteristics and the iris characteristics.

19. The computer-implemented system of claim 16, wherein the one or more operations further comprise:

presenting a notification in the VR scenario to notify the VR device user to perform biometric authentication.

20. The computer-implemented system of claim 16, wherein the one or more user interactions include a gesture, a body movement, or a body posture.

* * * * *